United States Patent [19]

Ichinomiya et al.

[11] Patent Number: 4,942,884
[45] Date of Patent: Jul. 24, 1990

[54] PORTABLE BATTERY POWERED ELECTROMAGNETIC THERAPY APPLICATION

[75] Inventors: Tsutomu Ichinomiya; Tomohiro Kami, both of Hikone; Fumio Kitagawa, Neyagawa; Sumio Wada, Hikone; Hideaki Abe, Moriguchi; Youichi Ise, Hirakata; Toshio Kusunoki, Hikone, all of Japan

[73] Assignee: Matsushita Electric Works, Ltd., Japan

[21] Appl. No.: 362,936

[22] Filed: Jun. 8, 1989

Related U.S. Application Data

[62] Division of Ser. No. 178,583, Apr. 7, 1988.

[30] Foreign Application Priority Data

Jun. 15, 1987 [JP] Japan .................................. 62-148534

[51] Int. Cl.⁵ .............................................. A61N 1/40
[52] U.S. Cl. ...................................... 128/804; 128/422
[58] Field of Search ........... 128/798, 802, 804, 419 R, 128/419 F, 422; 600/10, 13–15

[56] References Cited

U.S. PATENT DOCUMENTS

| 2,882,904 | 4/1959 | Rasmussen | 128/798 |
|---|---|---|---|
| 3,270,746 | 9/1966 | Kendall et al. | |
| 3,473,859 | 10/1969 | Kircher | |
| 4,197,851 | 4/1980 | Fellus | 128/798 |
| 4,456,001 | 6/1984 | Pescatore | 128/802 |
| 4,471,787 | 9/1984 | Bentall | 128/804 |
| 4,550,714 | 11/1985 | Talish et al. | 128/802 |
| 4,574,809 | 3/1986 | Talish | 128/419 F |

FOREIGN PATENT DOCUMENTS

| 2547949 | 4/1977 | Fed. Rep. of Germany . | |
| 2748780 | 5/1978 | Fed. Rep. of Germany . | |
| 2106394 | 4/1983 | United Kingdom | 128/804 |
| 8001045 | 5/1980 | World Int. Prop. O. | 128/804 |

Primary Examiner—Lee S. Cohen
Attorney, Agent, or Firm—Stevens, Davis, Miller & Mosher

[57] ABSTRACT

An improved portable battery powered therapy applicator which applies a high frequency electromagnetic field to a living tissue for promoting hematogenous effects. The applicator is in use to be attached to the skin of a patient and has a casing encapsulating therein, in addition to the battery, an antenna for directing the high electromagnetic field and electronic components forming an oscillator which energizes the antenna. These parts are mounted on a substrate which is made of a rigid material sufficient to resist deflection or deformation in order to protect the antenna on the substrate from deforming or receiving considerable stress at the time of detaching the applicator from the skin. Thus, the antenna can be kept free from breaking even through repeated operations of detaching the applicator, greatly enhancing reliability and prolong an operation life of the applicator.

14 Claims, 11 Drawing Sheets

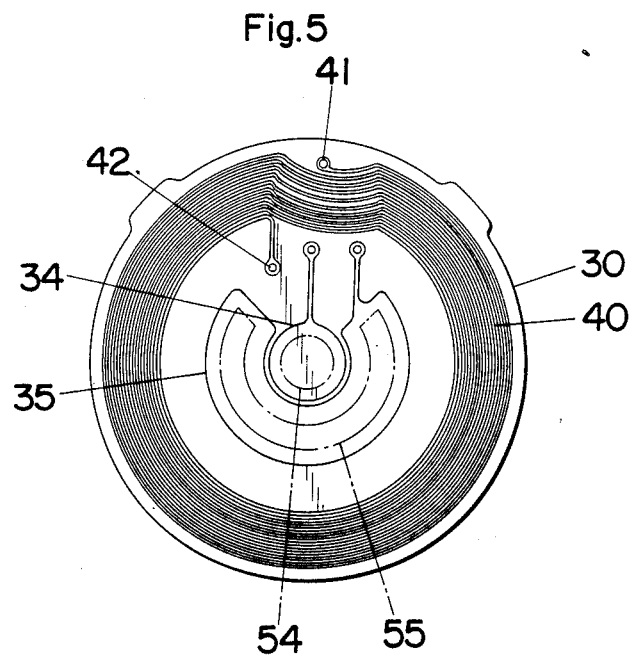
Fig.5
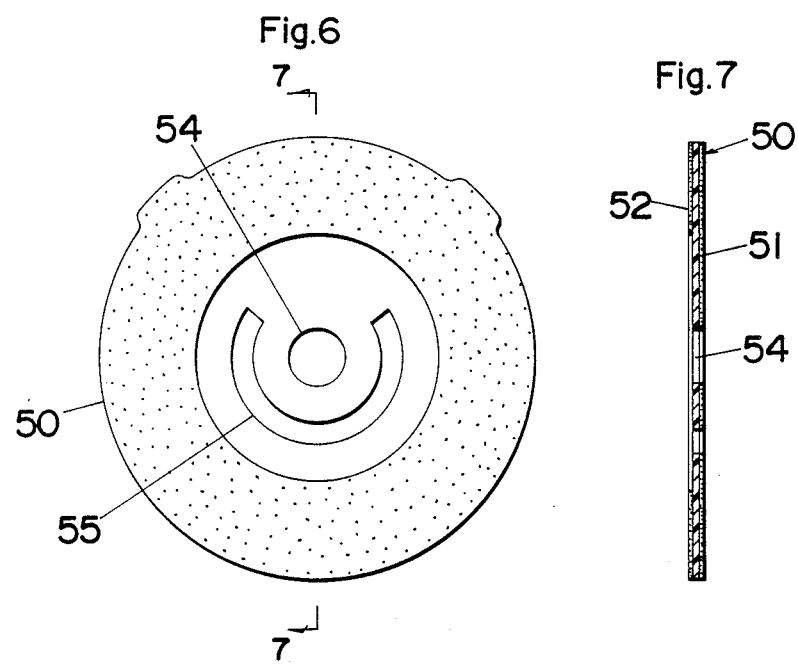
Fig.6
Fig.7

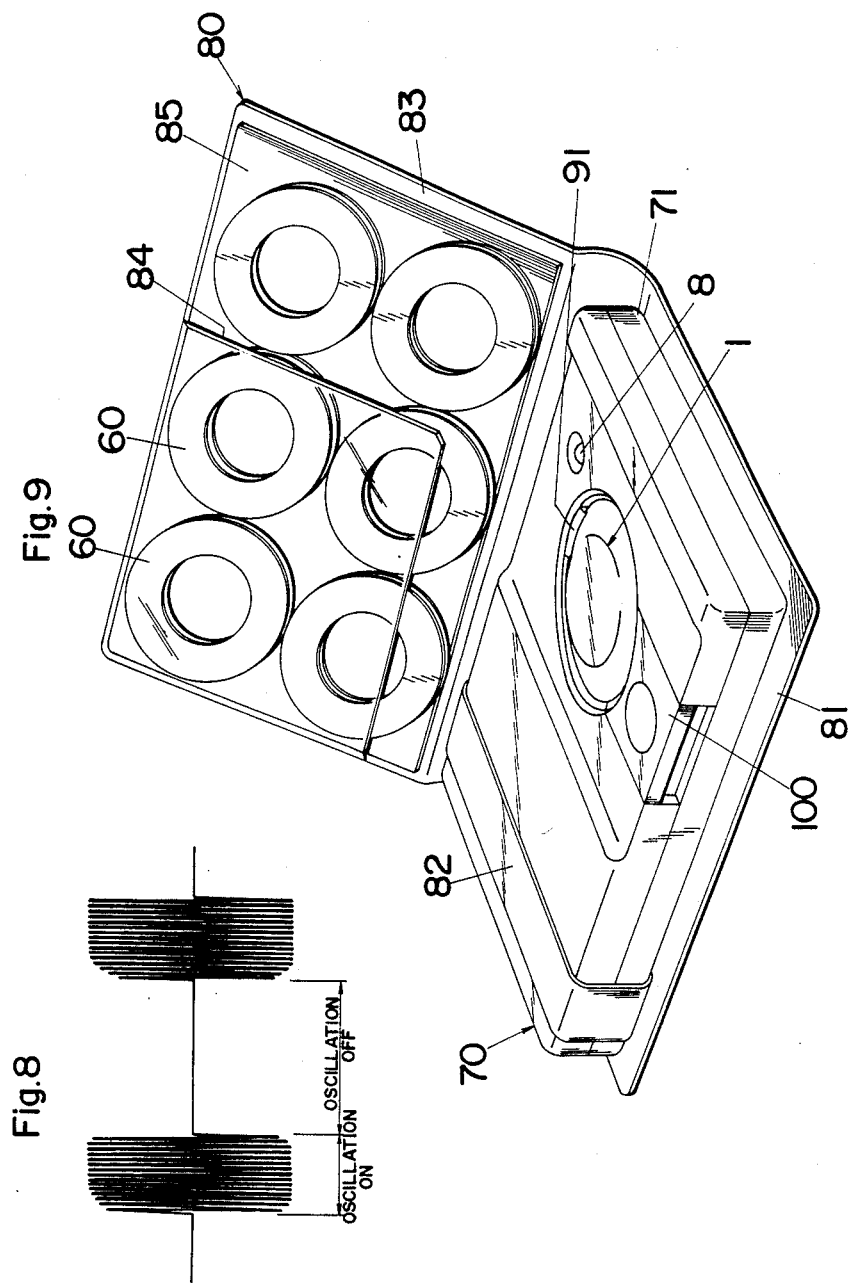

Fig.12
Fig.13
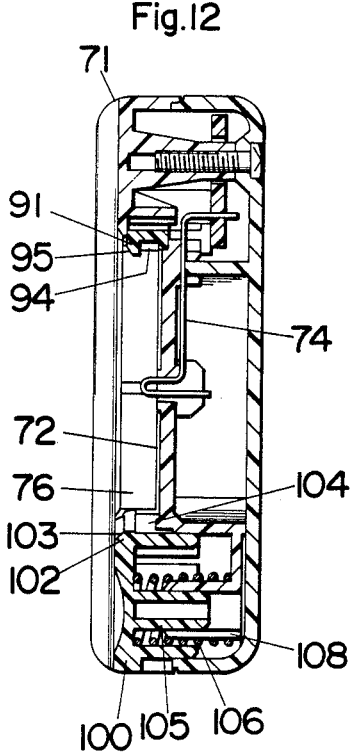
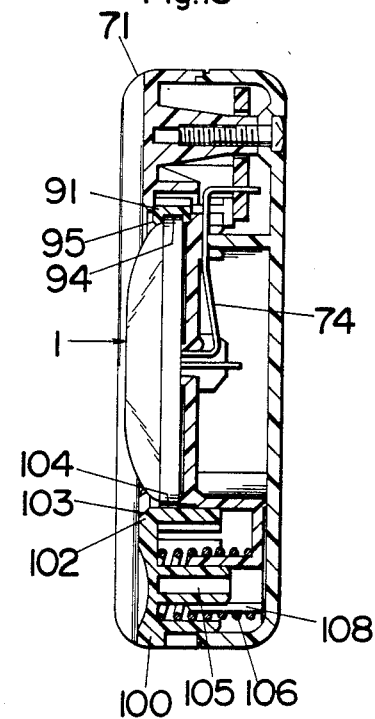

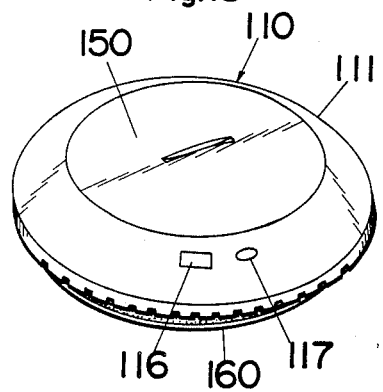
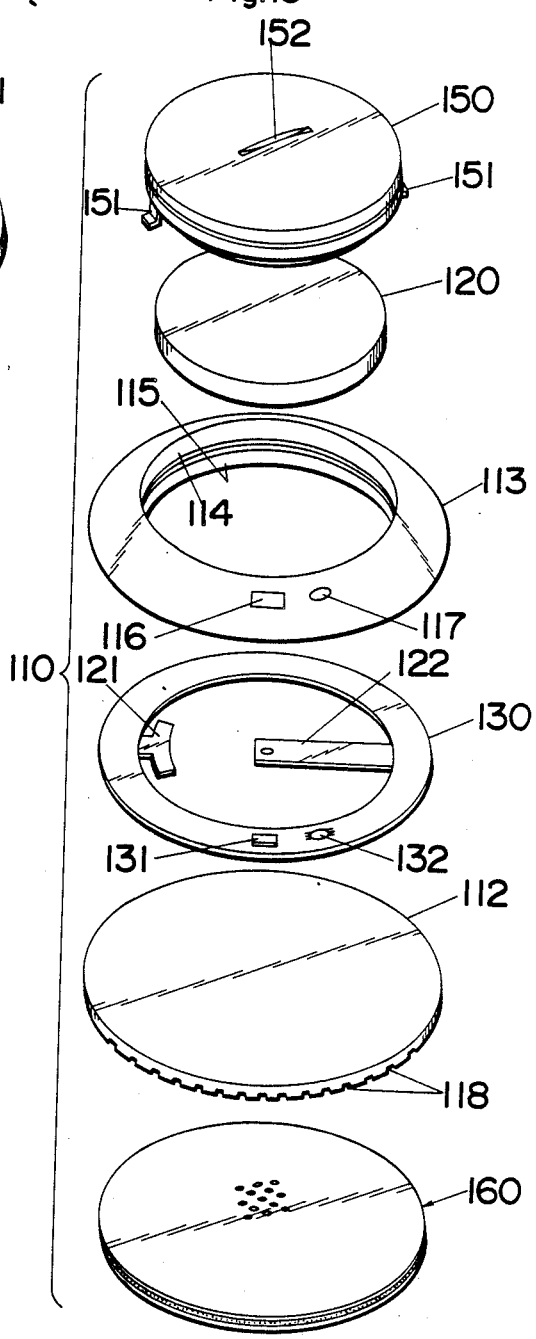

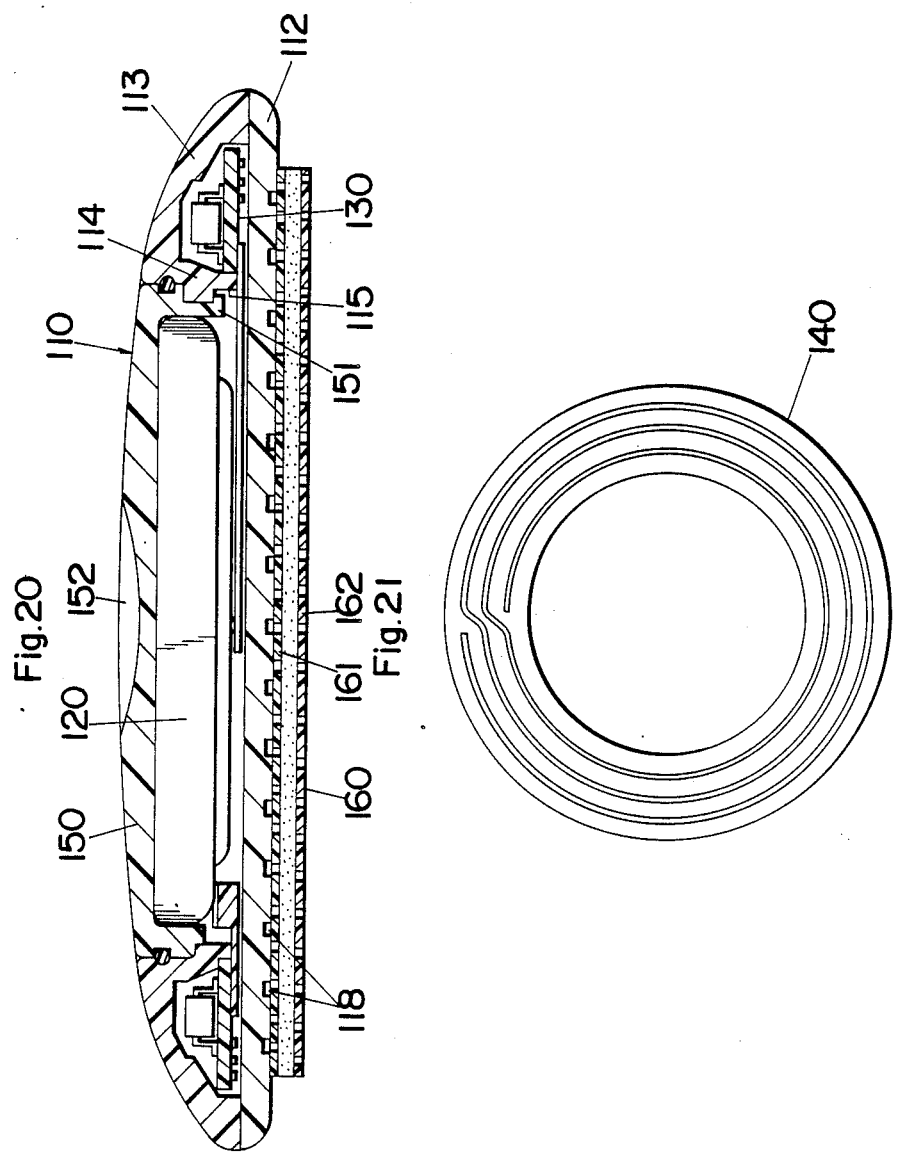

PORTABLE BATTERY POWERED ELECTROMAGNETIC THERAPY APPLICATION

This is a divisional of application Ser. No. 178,583, filed Apr. 7, 1988.

BACKGROUND OF THE INVENTION

1. Field of the Invention

The present invention is directed to a portable battery powered high frequency electromagnetic therapy applicator adapted in use to be attached to the skin of a patient for promoting hematogenous effects to the living tissue.

2. Description of the Prior Art

Battery powered high frequency electromagnetic therapy applicators are known as disclosed in U.S. Pat. No. 4,471,787. The applicator of this patent comprises a substrate mounting thereon a battery, a circuit for producing a high frequency electromagnetic field, and an antenna directing the electromagnetic field. The substrate is made resilient so that it is capable of conforming to the shape of the skin of a patient. However, the resiliency of the substrate brings about a drawback that the antenna mounted on the substrate is subject to a considerable stress as it is resiliently deformed during the repeated operations of attaching and detaching the applicator. Thus, the applicator of this patent is not expected to have an extended operating life.

SUMMARY OF THE INVENTION

In view of the above drawback, the present invention provides an improvement on a battery powered therapy applicator which assures an extended operating life. The applicator comprises a battery and an oscillator powered by the battery to produce a high frequency electromagnetic field which is transmitted through an incorporated antenna to a living tissue for promoting hematogenous effects. The battery as well as electronic components forming the oscillator are mounted on a substrate which is rigid enough free from substantial warping which would otherwise occur each time the applicator is detached from the skin of the user. This prevents the antenna on the substrate from suffering from repeated stress and therefore prevent it from breaking.

Accordingly, it is a primary object of the present invention to provide a battery powered therapy applicator of which antenna is kept intact during the repeated operations of detaching the applicator to thereby enhance reliability and extend an operating life.

The antenna is disposed on the undersurface of the substrate, while the battery is located centrally on the uppersurface of the substrate. The electronic components forming the oscillator are arranged on the uppersurface of the substrate around the battery for effective utilization of the space within the applicator. The antenna is preferably provided in the form of a spirally wound coil to have an elongated overall length within a limited space for obtaining an increased output energy at a minimum power consumption, which is most suitable for the battery powered applicator.

The applicator casing is composed of a bottom plate and a cover which are bonded at their peripheries with the periphery of the substrate clamped therebetween. The clamped portion is hermetically sealed to prevent the entry of fluid or vapor for keeping the applicator sanitary, which is therefore a further object of the present invention.

Formed in the outer surface of the bottom plate are a plurality of ventilation channels which face the skin of the user and permit the perspiration induced at the skin to escape outwardly therethrough from the undersurface of the applicator, ensuring a continued use of the applicator on the skin without accumulating the droplets of the perspiration.

Therefore, it is a further object of the present invention to provide a therapy applicator which can be attached on the skin of a patient in a comfortable manner.

The applicator in a preferred embodiment of the present invention is characterized to utilize a rechargeable battery which receives a charging current from a complementary charger unit. To this end, the charger unit has a recess into which the applicator is set to be recharged from a source of power in the charger unit. Formed on the bottom exterior of the applicator casing are a pair of electrodes which are in electrical contact respectively with complementary terminals on the bottom of the recess for electrical interconnection between the rechargeable battery in the applicator and the source of power in the charger unit. The electrodes comprises a center electrode concentric with the center of the applicator casing and an outside electrode extending circumferentially about the center electrode. The applicator is round-shaped to have no particular orientation. For assuring constant contact of the respective electrodes with the terminals without paying undue attention to the orientation of the applicator when setting the applicator in the recess of the charger unit, unique arrangements are made to the terminals in the recess and the electrodes of the applicator. The terminals comprises a center terminal on the center of the recess bottom and a pair of outside terminals which are spaced at the same distance from the center terminal and are aligned therewith. The outside electrode extends circumstantially at an angular range of more than 180° about the center electrode so that at least one of the outside terminals can always comes into contact with the outside electrode irrespective of the angular orientation at which the applicator is set into the recess.

It is therefore a further object of the present invention to provide a therapy applicator which can be set into the charger unit for the recharging purpose without requiring a special attention as to the angular orientation of the applicator.

The outside electrode is preferably in the form of an open loop so that the electromagnetic field will not induce an eddy current loss in the outside electrode although the outside electrode is in closely adjacent relation to the antenna, which is therefore a still further object of the present invention.

The charger unit is formed at the periphery of the recess with a latch member which is movable between a position of projecting into the recess and a position of retracting therefrom. The latch member is spring biased to the projected position at which the applicator has its peripheral edge engaged into a groove formed in the latch member so as to retain the applicator within the recess. Upwardly of the groove the latch member is formed with a downwardly inclined taper edge for abutment against the peripheral edge of the applicator being inserted in the recess. By this abutment, the latch member is pushed back to the retracted position of allowing the peripheral edge to ride over the taper edge for engagement into the groove. Thus, the applicator can be easily guided into the recess and retained therein for prevention of accidental removal of the applicator. An eject button is also provided at the periphery of the recess and is made vertically movable. The edge of the eject button extends arcuately and fit in a notched portion of the peripheral wall of the recess to be in direct engageable relation to the peripheral edge of the applicator such that when the eject button is depressed the arcuate edge of the eject button passes over the peripheral edge of the applicator into engagement with the bottom surface thereof. Upon being released, the eject button returns upwardly by a bias force to lift the applicator on the upwardly returning edge thereof, making it ready to remove the applicator from the recess by the fingers of the user.

In addition to the above, the present invention discloses other advantageous features including the circuit arrangement of the rechargeable applicator that a control circuit is included in the applicator. The control circuit is operative to cease producing the electromagnetic field upon detection of the presence of an external voltage supplied from the charger unit or detection of the voltage level of the rechargeable battery dropping to a predetermined level. Also the control circuit is operative to stop recharging either when a full charged condition is reached or when the recharging is made for over a predetermined time.

These and still other advantages and objects will be more apparent from the following description of the present invention when taken in conjunction with the attached drawings.

BRIEF DESCRIPTION OF THE DRAWINGS

FIG. 5 is a bottom view of the therapy applicator with its bottom sealing sheet removed;

FIG. 6 is a bottom view of the sealing sheet;

FIG. 7 is a cross section taken along line 7—7 of FIG. 6;

FIG. 8 is a waveform chart of high frequency pulses produced at the applicator;

FIG. 9 is a perspective view of a charger unit for recharging the therapy applicator;

FIG. 12 is a cross section taken along line 12—12 of FIG. 10;

FIG. 13 is a sectional view similar to FIG. 12 but with the applicator shown in the set position in the charger unit;

FIG. 18 is a perspective view of a therapy applicator in accordance with a second embodiment of the present invention;

FIG. 19 is an exploded perspective view of the therapy applicator of FIG. 18;

FIG. 20 is a sectional view of the applicator; and

FIG. 21 is a plan view of an antenna used in the applicator.

DESCRIPTION OF THE PREFERRED EMBODIMENTS

Figure 1:
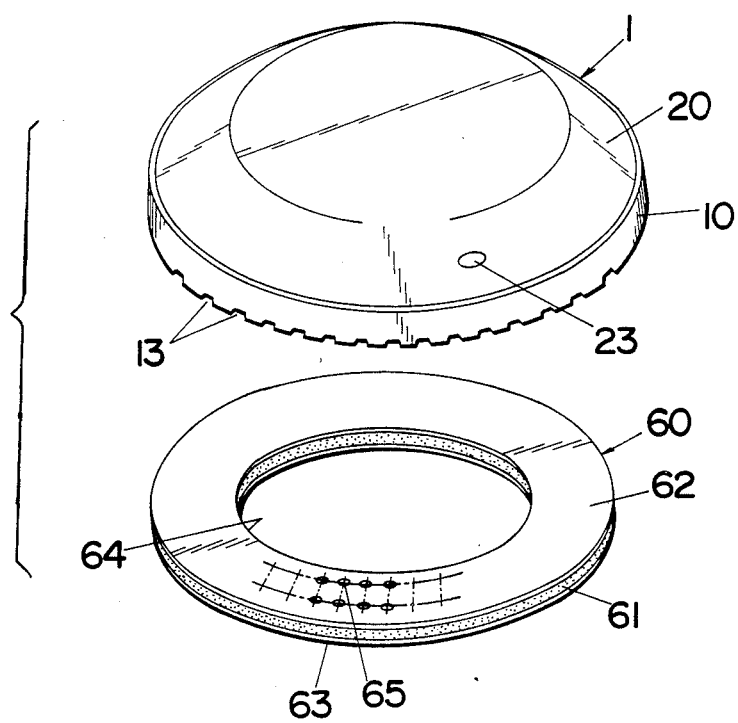
FIG. 1 is a perspective view of a high frequency therapy applicator in accordance with a first embodiment of the present invention.
Figure 2:
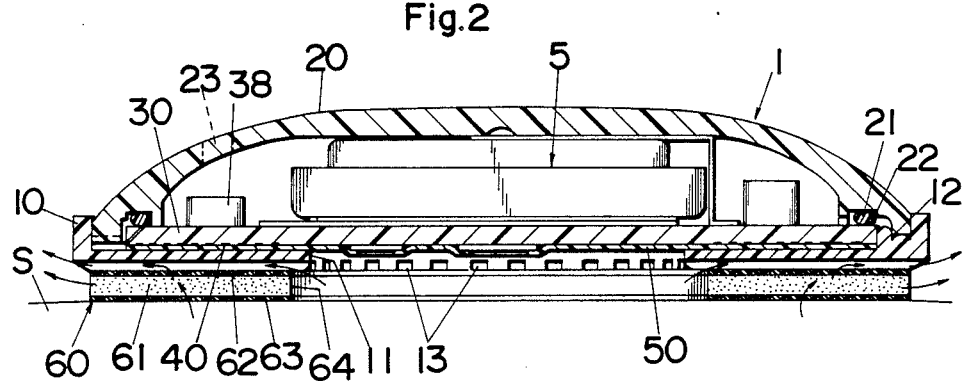
FIG. 2 is a vertical section of the therapy applicator.

Referring to FIGS. 1 and 2, there is shown a portable battery powered electromagnetic therapy applicator 1 in accordance with a first preferred embodiment of the present invention, which operates to apply a high frequency electromagnetic field to living tissue for promoting hematogenous effects. The applicator 1, which is configured into a generally flat disk with a rounded top having a diameter of approximately 30 mm, is adapted in use to be attached by means of a disposable adhesive pad 60 to a desired area of the patient. As shown in FIG. 2, the applicator comprises a bottom plate 10 and a top cover 20 fitted thereon to encapsulate therebetween a rechargeable battery 5 and a substrate 30 carrying thereon an antenna 40 for transmitting the high frequency electromagnetic field. The substrate 30 is provided as a printed board with a print pattern on either side. One printed pattern 31 on the upper surface of the substrate 30 provides the interconnections for electronic components such as an IC chip 32 which are mounted to form an oscillating circuit for producing the high frequency magnetic field to be transmitted through the antenna 40. The other printed pattern on the undersurface of the substrate 30 constitutes the antenna 40 of a dense coiled configuration on the peripheral area thereof, as seen in FIG. 5. The substrate 30 or the printed board is made from a glassfibre reinforced plastic material to be rigid enough to resist deformation, whereby protecting the antenna 40 mounted thereon from suffering from such deformation or stress which might lead to the breakage of the antenna 40. The antenna 40 is connected at respective terminals 41 and 42 to the oscillator circuit on the upper surface of the substrate 30. Also printed on the undersurface of the substrate 30 are a center electrode 34 and an arcuately shaped outside electrode 35 extending over an angular range of 180° about the center terminal 34, or at approximately 270° angular range. These electrodes 34 and 35 are connected through corresponding lugs 36 and 37 on the substrate 30 to the opposite poles of the rechargeable battery 5 for effecting the recharging by an external charger unit 70, the detail of which will be explained hereinafter.

Figure 4:
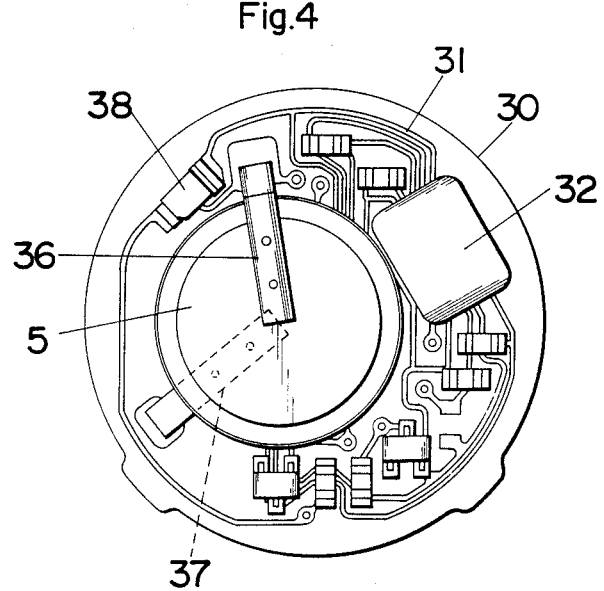
FIG. 4 is a top view of the therapy applicator with its cover removed.

The bottom plate 10 receiving thereon the substrate 30 is provided with a center opening 11 in which the electrodes 34 and 35 on the substrate 30 are exposed. Interposed between the bottom plate 10 and the substrate 30 is an electrically insulative sealing sheet 50 which is made of a thin plastic material. The sheet 50 has on its both faces adhesive layers 51 and 52 by which the sheet 50 is secured to the complementary surfaces of the bottom plate 10 and the substrate 30 for effecting water-tight sealing therebetween. As shown in FIGS. 6 and 7, the sheet 50 is formed with a center hole 54 and an arcuate slot 55 which correspond respectively to the center electrode 34 and the outside electrode 35 on the substrate 30 but has a less diameter and a less width than those, as seen in dotted line of FIG. 5. With this arrangement, enlarged contact faces can be provided between the edge portions the center hole 54 and the center electrode 34 and between the edge portions of the slot 55 and the arcuate electrode 35, assuring firm adhesion therebetween preventing spurious peeling of the sheet 50 from these edge portions. The adhesive layer 51 is formed on the entire upper surface of the sheet 50 for completely clog the throughholes in the substrate 30 as well as for covering the antenna 40, maintaining the substrate 30 in sealed condition to prevent the entry of perspiration and other fluids and thus prevent the proliferation of germs in the applicator 1. As seen in FIG. 4, the battery 5 is centrally mounted on the substrate 30 to leave therearound sufficient space for mounting the electronic components forming the oscillator circuit by effectively utilizing available space.

The bottom plate 10 is formed on its upper surface with a peripheral groove 12 into which the peripheral edge of the top cover 20 engaged, as seen in FIG. 2., and is hermetically sealed to the bottom plate 10 by the known supersonic sealing technique. In addition, an 0-ring 21 is received in a furrow 22 formed inward of the peripheral edge of the top cover 20 to be in sealing contact with the marginal portion of the substrate 30 for completely sealing the electronic circuits on the substrate 30. The circuit formed on the substrate includes a light emitting diode (LED) 38 operative to produce visible light repetitively until the battery 5 drops to a predetermined voltage level, which light is visible through a window 23 formed in the top cover 20. The top cover 20 is made of a transparent material and has an opaque coating on its inside surface except for a portion which defines the window 23.

Figure 3:
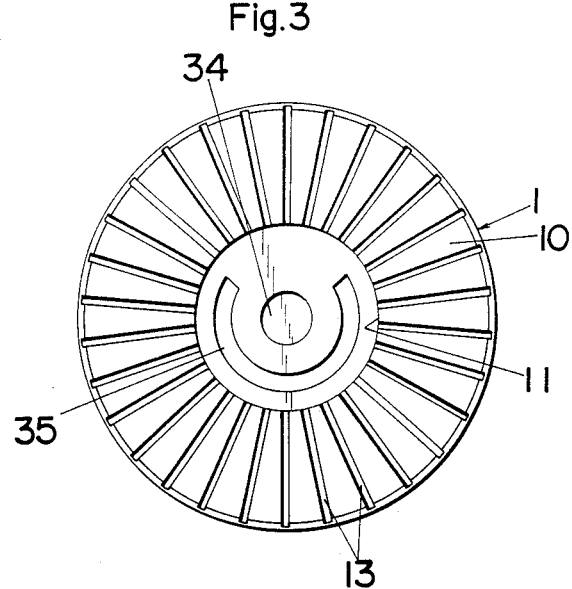
FIG. 3 is a bottom view of the therapy applicator.

The therapy applicator 1 is in use to be attached to a portion of the body to be treated by means of the removable adhesive pad 60. As shown in FIGS. 1 and 2, the adhesive pad 60 is provided in the form of a ring 61 with an adhesive layer on either face thereof, one adhesive layer 62 for adhesion to the under surface of the bottom plate 10 and the opposite adhesive layer 63 for adhesion to the skin S of the patient. The ring 61 or the core material of the adhesive pad 60 is made from a flexible and air permeable material such as foamed polyurethane and is shaped to coincide its center aperture 64 with the center opening 11 of the bottom plate 10. Each of the adhesive layers 62 and 63 is formed to have a plurality of uniformly disposed tiny air vents 65 which allow the ventilation of perspiration induced on the treated surface of the skin. In this connection, the bottom plate 10 is formed in its outer surface with a plurality of radial channels 13 each of which, as best shown in FIG. 3, runs the full radial distance from the circumference of the center opening 11 to the outer peripheral edge of the bottom plate 10. Thus, the perspiration or vapor on the skin surface can be allowed to be directed into radial channels 13 either through the adhesive pad 60 or through the center opening 11 and is successfully ventilated outwardly through the channels 13. Further the perspiration or vapor can be routed through the adhesive pad 60 itself into the air. These escape flows are indicated by arrows in FIG. 2. The above ventilation arrangement enables the continued use of the applicator without accumulating the droplets of perspiration and therefore without causing rashes on skin. Further with the provision of the radial channels 13, the adhesive pad 60 can be easily peeled off from the bottom plate 10 by piercing the nail of the user into the outer end of the channel 13, enhancing the convenience of replacing the adhesive pad 60.

Figure 10:
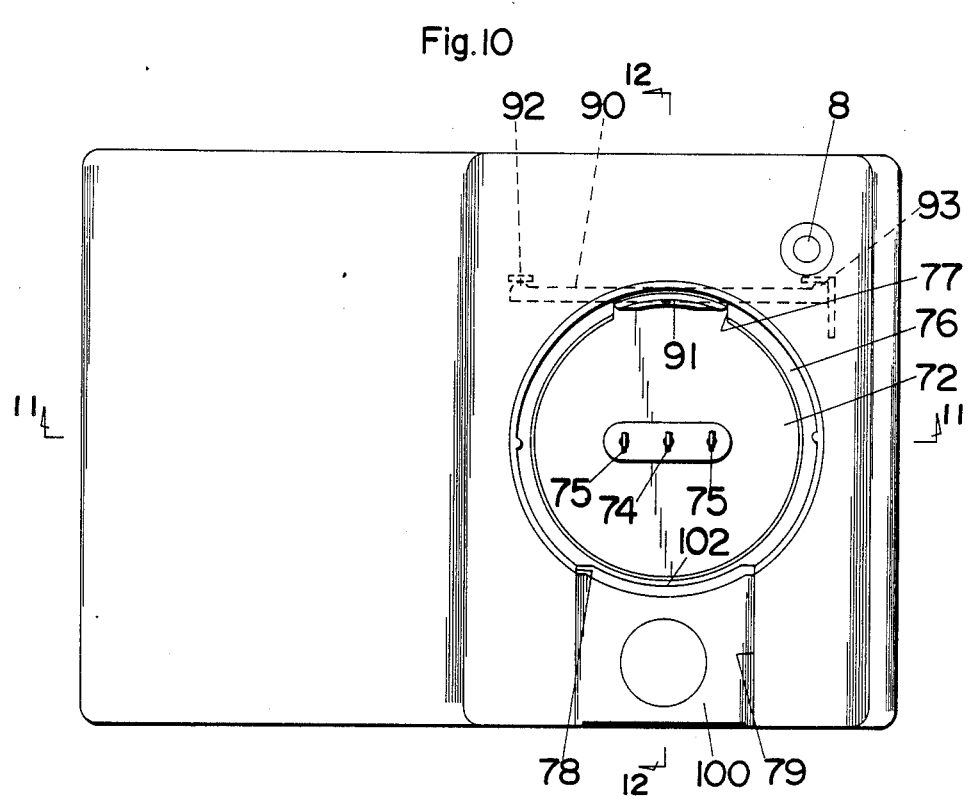
FIG. 10 is a top view of a charger unit.
Figure 11:
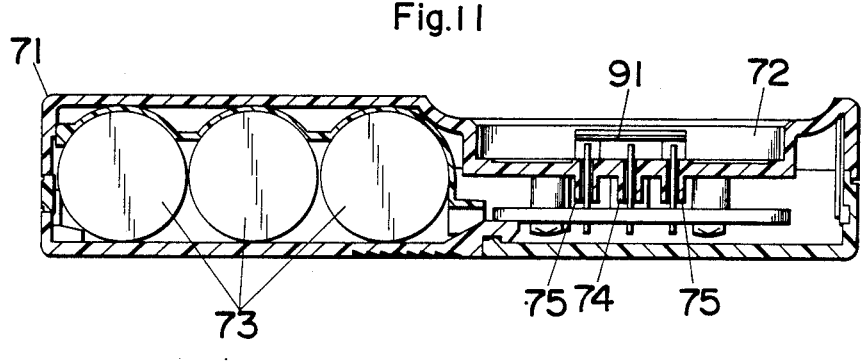
FIG. 11 is a cross section taken along line 11—11 of FIG. 10.

Referring to FIGS. 9 and 10, the charger unit 70 for recharging the therapy applicator 1 is shown to comprise a flat rectangular casing 71 with a circular recess 72 for detachably receiving the applicator 1. The charger casing 71 is held on a foldable covering 80 with its one end inserted in a holder loop 82 on one flap 81 of the covering 80 and with the other end secured on the same flap 81 by means of a snap closure (not seen). The other flap 83 includes a pocket 84 for a retainer sheet 85 carrying thereon a number of fresh adhesive pads 60 to be attached to the applicator 1.

The charger casing 71 accommodates dry batteries 73 as a power source for recharging the battery 5 in the applicator 1. Projected on the bottom of the recess 72 are a series of three terminal pins 74 and 75 for electrical contact with the center electrode 34 and the outside electrode 35 on the bottom of the applicator 1 received in the recess 72. These terminal pins 74 and 75 are equally spaced and aligned horizontally with one terminal pin 74 located at the center of the recess 72. The center terminal pin 74 is connected within the casing 71 to one end of the power source while the other two terminal pins 75 are together connected to the other end of the power source. It should be noted at this time that since the arcuate electrode 35 extends over a angular range of 180° about the center electrode 34, as described with reference to FIG. 5, at least one of the terminal pins 75 can be kept in electrical contact with the arcuate electrode 35 irrespective of the angular orientation of the applicator 1 received in the recess 72, ensuring the constant electrical connection between the applicator 1 and the charger unit 70. In this connection, the arcuate electrode 35 is advantageous in preventing eddy current loss which could be otherwise developed under the effect of the high frequency field from the antenna 40 if the terminal 35 were formed in the form of a closed loop conductive elements. The terminal pins 74 and 75 are spring biased upwardly into the projected position on the bottom of the recess 72 where they are in positive contact engagement with the corresponding electrodes on the bottom of the applicator 1 for the recharging purpose.

The recess 72 is formed in its circular peripheral wall 76 with diametrically opposed first and second arcuate notches 77 and 78, the second notches 78 having a greater circumferential length than the first notch 77. The first notch 77 receives an arcuate latch 91 formed at the center of a resilient strip 90 is supported at its longitudinal ends 92 and 93 within the casing 71. The latch 91 is biased by the resiliency of the strip 90 to project slightly into the recess 72, as shown in FIGS. 10 and 12, and is formed with a first groove 94 which is open to the recess 72 and receives therein the peripheral edge of the applicator 1, as shown in FIG. 13. The second notch 78 is open to an indent 79 which is formed in the upper wall of the casing 71 and receives therein an eject button 100. The eject button 100 is shaped to have an arcuate inner wall which is positioned in the second arcuate notch 78 to complete the peripheral wall of the recess 72 in cooperation with the latch 91. Projecting inwardly from the upper end of the arcuate wall is a jaw 102 which defines therebelow a second groove 104 for retaining therein the peripheral edge of the applicator 1 at the portion diametrically opposed to the latch 91, as shown in FIG. The eject button 100 is mounted with its downwardly extending stem 105 into a hollow stud 108 in the casing 71 to be vertically movable therealong and is biased upwardly by a spring 106 to an upward position of retaining the peripheral edge of the applicator 1 in the second groove 104.

When the applicator 1 needs to be recharged, it can be easily set into the recess 72 of the charger 70 as the latch 91 is pushed in by the peripheral edge of the applicator 1 to permit the opposed peripheral edge to ride over the jaw 102 of the eject button 100 into engagement with the second groove 104, after which the latch 91 is resiliently urged inwardly to engage the peripheral edge of the applicator 1 into engagement with the first groove 94. Provided on the upper ends of the latch 91 and the jaw 102 is an inwardly inclined taper brims 95 and 103 which serve to facilitate the insertion of the applicator 1 into the recess 72. When the applicator 1 is put with its peripheral edge firstly engaged only at one portion into the first groove 94 of the latch 91 but with the opposed portion left resting on the jaw 102, further pressing in of the applicator 1 will cause the opposite portion of the peripheral edge to easily slip over the inclined brim 103 of the jaw 102 into engagement with the second groove 104 as pushing the 91 radially outwardly. In the opposite case when the applicator 1 is put with its peripheral edge firstly engaged only into the second groove 104 behind the jaw 102 while left resting on the latch 91, the peripheral edge of the applicator 1 on the latch 91 can easily ride over the taper brim 95 into engagement with the first groove 94 as resiliently pushing back the latch 91 by the like pressing in of the applicator 1.

Figure 14:
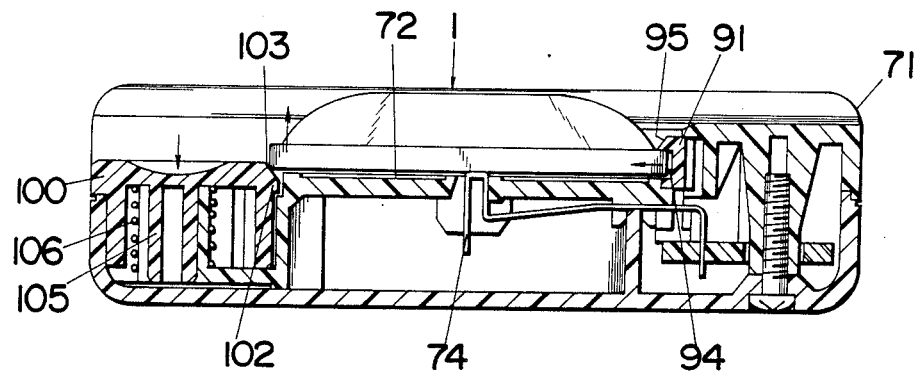
FIGS. 14 and 15 are sectional views illustrating the removal of the applicator from the charger unit.
Figure 15:
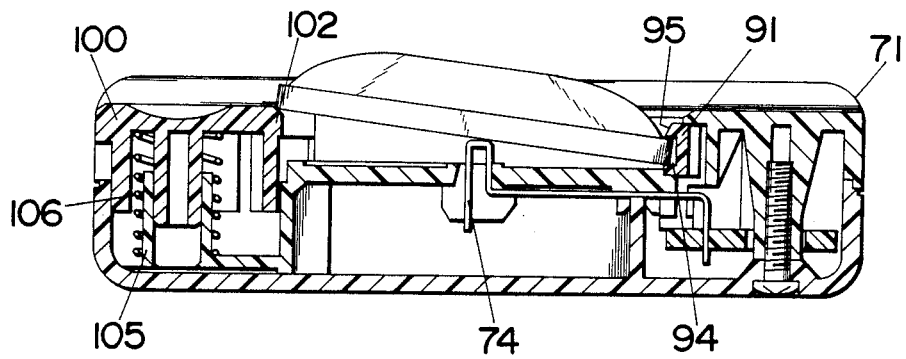

The applicator 1 thus placed in the recess 72 is kept in the recharge condition until the eject button 100 is pressed. After the applicator 1 is recharged to an enough level, it is popped out by simply pressing down the eject button 100. As the eject button 100 is pressed down from the position of FIG. 14 to the position of FIG. 15, the applicator 1 is moved under the effect of the return bias of the latch 91 to the left of the FIG. 14 at which the one portion of the peripheral edge thereof rides on the taper brim 103 of the jaw 102 of the lowered eject button 100 while the opposite portion of the peripheral edge is disengaged from the first groove 94. During this movement, the applicator 1 also receives the upward bias from each of the terminal pins 74 and 75 to be thereby lifted slightly, assisting the peripheral edge to ride on the taper brim 103 and at the same time to be disengaged from the first groove 94. Upon subsequent release of the eject button 100, the button 100 returns upwardly by the bias of the spring 106 to thereby lift up the one peripheral edge of the applicator 1 on the upwardly moving jaw 102, thus popping the applicator 1 substantially outwardly of the recess 72, as shown in FIG. 15, and permitting the easy access to the applicator 1 by the fingers of the user. Thus, the applicator 1 can be readily picked out from the charger unit 70 by the fingers to be ready for use on the portion of the body to be treated.

Figure 16:
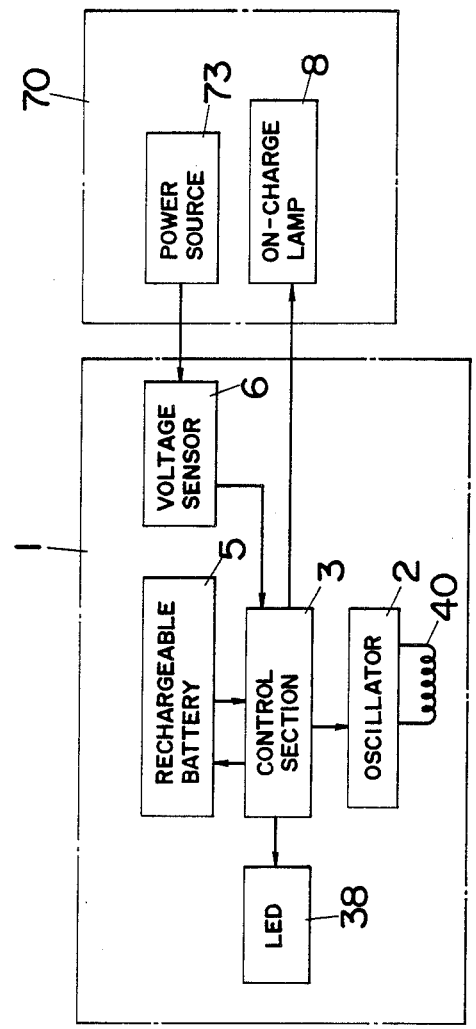
FIG. 16 is a block circuit diagram of the applicator and the charger unit.
Figure 17:
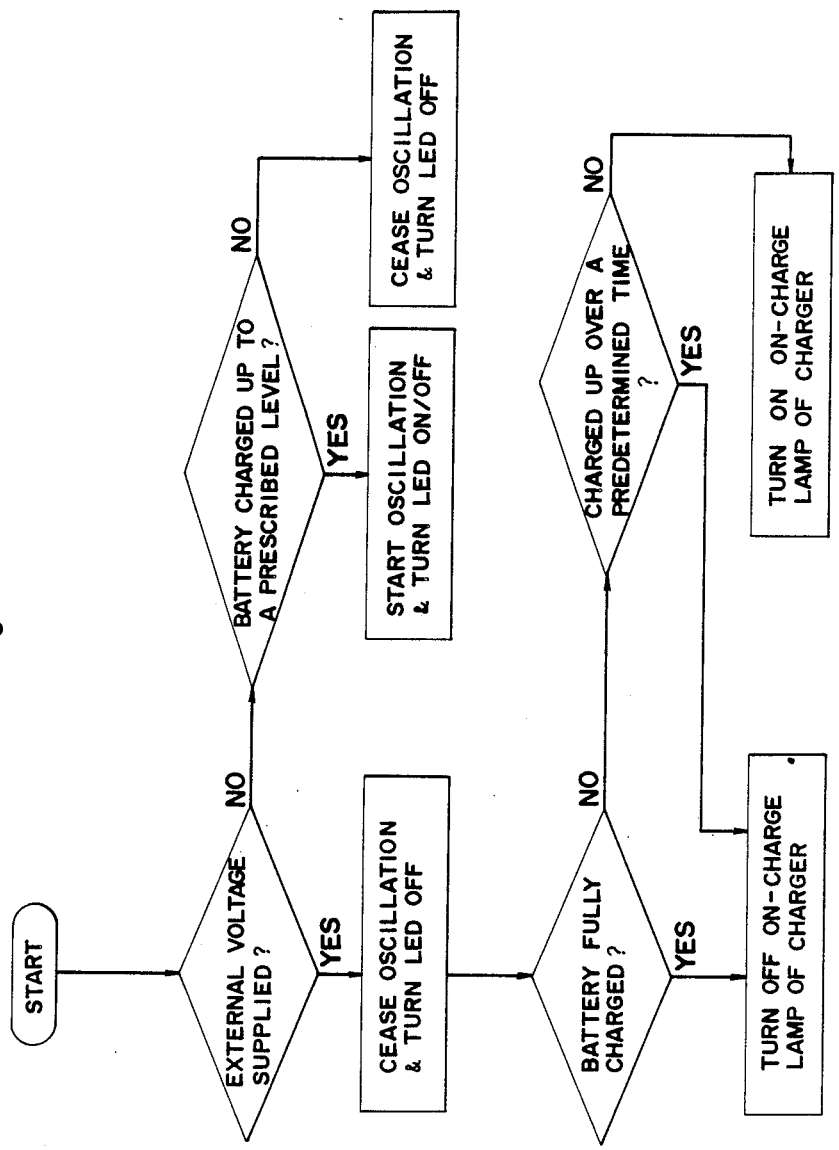
FIG. 17 is a flow chart illustrating the operation of the applicator and the charger unit.

The circuits and the operations of the applicator 1 and the charger 70 are explained with reference to FIGS. 16 and 17. As shown in the block diagram of FIG. 16, the circuit of the applicator 1 includes an oscillator 2 which is powered by the rechargeable battery 5 to produce a high frequency electromagnetic filed at a frequency range of 9 MHz which is transmitted through the antenna 40. The oscillator is controlled by a control section 3 to occur repetitively at a time interval of 1200 microseconds and last a short time period of 400 microseconds, as shown in FIG. 8. The LED 38 of the circuit is also controlled by the control section 3 to repeat turning on and off during the energization of the antenna 40 at a suitable cycle for indicating that the oscillation of the high frequency electromagnetic field is being produced. Further, the control section 3 is operative to monitor through a voltage sensor 6 the external voltage supply from the charger unit 70 as well as the voltage level of the battery 5 so as to cause the oscillator 2 to operate only when the external voltage is not supplied and the voltage level of the battery 5 is above a predetermined value, as seen from the operation sequence of FIG. 17. When the voltage is supplied from the charger unit 70, or the applicator 1 is set into the recess 72 of the charger unit 70, the control section 3 responds to cease the operation of the oscillator 2 and permits the applicator 1 to be recharged. During the charging process, the control section 3 sends to the charger unit 70 a signal which keeps an on-charge lamp 8 turned on until the battery 5 is charged up to a predetermined level (full charged level) or it has been charged over a predetermined period of time. When either of the above is detected, the control section 3 acts to terminate the recharging process for prevention of over-charging and at the same time to turn off the on-charge lamp 8 for notifying the completion of the recharging.

Referring to FIGS. 18 to 21, there is shown a therapy applicator 110 powered by an incorporated dry battery 120. The applicator 110 comprises a disk-shaped casing 111 composed of a bottom plate 112 and an annular cover 113 which are both made form the plastic material and bonded by the known supersonic welding technique. The annular cover 113 is secured on the periphery of the bottom plate 112 to form outwardly of a depending inner wall 114 a space for receiving a ring-shaped substrate 130 and to form inwardly thereof a space for receiving the dry battery 120. The substrate 130 is made from a fiber reinforced plastic material to be stiff enough to resist deformation and it is provided as a doublesided printed board with conductor lines on the upper surface and with a coiled antenna 140 on the undersurface thereof. Mounted on the substrate 130 are a number of electronic components which are interconnected by the conductor lines to form a like electronic circuit for energizing the antenna 140. The circuit responsible for producing a like high frequency electromagnetic field is identical in operation to that of the previous embodiment except that it involves no recharging function. The circuit includes a power switch 131 which is mounted on the substrate 130 and is accessible through a membrane actuator 116 formed in the annular cover 113. A LED 132 is also formed in the circuit which is viewed through a window 117 in the annular cover 113. Extending inwardly from the undersurface of the substrate 130 are first and second terminal strips 121 and 122 which are in contact respectively with the opposite electrodes of the dry battery 120 for electrical connection between the circuit and the battery 120. A battery lid 150 is placed over the battery 120 and is removably engaged at its hooks 151 with undercuts 115 in the depending wall 114, as shown in FIG. 20. The lid 150 has a coin slot 152 for facilitating the closure and opening of the rid 150 by the use of a coin. The applicator 110 is adapted on the skin of the patient with the aid of a like adhesive pad 160 of an air permeable material with air permeable adhesive layers 161 and 162 on the opposite faces. The outer bottom surface of the bottom plate 112 is formed with a number of air ventilating channels 118 for escaping perspiration induced behind the pad 160 outwardly of the applicator 110, in the like fashion as in the previous embodiment.

What is claimed is:

1. A portable battery powered diathermy therapy applicator adapted for use on the skin of a patient for applying a high frequency electromagnetic field to a living tissue comprising:
   an oscillator for producing the high frequency electromagnetic field;
   an antenna connected to and energized by said oscillator to transmit the electromagnetic field to the living tissue;
   a battery connected to and driving the oscillator; and
   a substrate mounting thereon said antenna, said battery and electrical components forming the circuit of said oscillator;
   a flat casing accommodating therein said substrate carrying said antenna, said battery and said electrical components, and support means for attaching said casing onto the skin of the user;
   said flat casing being circular in planar configuration and having a top with a rounded periphery.

2. A portable battery powered diathermy applicator as set forth in claim 1, wherein said flat casing has a bottom and said support means comprises an adhesive pad having adhesive layers on its opposite faces, said casing being held on the skin of the user with one of the adhesive layers adhered to the bottom of said casing and the other adhesive layer to the skin of the user.

3. A portable battery powered diathermy applicator as set forth in claim 2, wherein said adhesive pad comprises a circular cushioning core member having said adhesive layers on its opposite faces.

4. A portable battery powered diathermy applicator as set forth in claim 3, wherein said core member is made of a porous and permeable material.

5. A portable battery powered diathermy applicator as set forth in claim 4, wherein said core member is in the form of a ring.

6. A portable battery powered diathermy applicator as set forth in claim 1, wherein said casing comprises a bottom plate and a cover which are bonded together at their outer peripheries with the periphery of said substrate clamped therebetween.

7. A portable battery powered diathermy applicator as set forth in claim 6, wherein an O-ring is held between the substrate and one of the cover and the bottom plate for effecting a water-proof sealing therebetween.

8. A portable battery powered diathermy applicator as set forth in claim 6, wherein a plastic sheet is interposed between the substrate and the bottom plate, said plastic sheet having adhesive layers on the opposite sides thereof for adhesion respectively to the substrate and the bottom plate to effect sealing therebetween.

9. A portable battery powered diathermy applicator as set forth in claim 8 wherein the peripheral edges of the bottom plate and the cover are hermetically sealed to each other by supersonic welding.

10. A portable battery powered diathermy applicator as set forth in claim 1, wherein said antenna is formed of a spirally placed conductor arranged in the periphery of said substrate.

11. A portable battery powered diathermy applicator as set forth in claim 1, wherein said flat casing has a bottom that is formed with a plurality of ventilation grooves by way of which any perspiration induced at the skin of the patient can escape outwardly from the bottom of the applicator casing.

12. A portable battery powered diathermy applicator as set forth in claim 1, including a light emitting diode connected to said oscillator and which emits light for indicating the actuation of said oscillator, said light emitting diode being viewed through a window in the casing, the casing being made of a transparent material to which an opaque finish is applied except for a portion so as to define said window at the non-finished portion.

13. A portable battery powered diathermy applicator as set forth in claim 1, including a light emitting diode connected in circuit with said oscillator, said light emitting diode driven to be repetitively turned on and off during the actuation of the oscillator for simulating the cyclic energization of the oscillator in which the oscillator takes place at a suitable time interval.

14. A portable battery powered diathermy applicator as set forth in claim 1, wherein said battery is a dry battery which is capable of being replaced through an opening formed in said flat casing, said opening being closed by a removable lid.

* * * * *